United States Patent [19]

Siuta et al.

[11] 4,185,032
[45] Jan. 22, 1980

[54] UREYLENE PHENYLENE ANIONIC NAPHTHALENESULFONIC ACIDS

[75] Inventors: Gerald J. Siuta, Yonkers; Ransom B. Conrow, Pearl River; John F. Poletto, Nanuet; Seymour Bernstein, New City, all of N.Y.

[73] Assignee: American Cyanamid Company, Stamford, Conn.

[21] Appl. No.: 923,744

[22] Filed: Jul. 11, 1978

[51] Int. Cl.$^2$ .................. C07C 143/30; A61K 31/185
[52] U.S. Cl. ............................ 260/506; 260/507 R; 424/315
[58] Field of Search ........................................ 260/506

[56] References Cited

U.S. PATENT DOCUMENTS 4,120,891  10/1978  Poletto et al. ........................ 260/506

OTHER PUBLICATIONS

Adams et al., J. Chem. Soc., pp. 3739–3744, (1956).

Primary Examiner—Nicky Chan
Attorney, Agent, or Firm—Claude J. Caroli

[57] ABSTRACT

Novel ureylenebis-[substituted-phenylenecarbonylimino-substituted-phenylenecarbonylimino-naphthalenetrisulfonic acid, alkali metal salts], useful as inhibitors of the complement system of warm-blooded animals, the amino-substituted phenylenecarbonylimino, substituted-phenylenecarbonylimino-naphthalenetrisulfonic acid, alkali metal salts, which are new intermediates for the preparation of the active ureylenes, and the process for their preparation.

10 Claims, No Drawings

UREYLENE PHENYLENE ANIONIC NAPHTHALENESULFONIC ACIDS

BACKGROUND OF THE INVENTION

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in the body processes can be found in, for example, Bull. World Health Org., 39, 935–938 (1968); Ann. Rev. Medicine, 19, 1–24 (1968); The John Hopkins Med. J., 128, 57–74 (1971); Harvey Lectures, 66, 75–104 (1972); The New England Journal of Medicine, 287, 452–454; 489–495; 545–549; 592–596; 642–646 (1972); Scientific American, 229, (No. 5), 54–66 (1973); Federation Proceedings, 32, 134–137 (1973); Medical World News, Oct. 11, 1974, pp. 53–66; J. Allergy Clin. Immunol., 53, 298–302 (1974); Cold Spring Harbor Conf. Cell Proliferation 2/Proteases Biol. Control/229–241 (1975); Ann. Review of Biochemistry, 44, 697 (1975); Complement in Clinical Medicine, Disease-a-Month, (1975); Complement, Scope, December 1975; Annals of Internal Medicine, 84, 580–593 (1976); "Complement: Mechanisms and Functions", Prentice-Hall, Englewood Cliffs, N.J. (1976); Essays Med. Biochem., 2, 1–35 (1976); Hospital Practice, 12, 33–43 (1977); Perturbation of Complement in Disease, Chap. 15 in Biological Amplification Systems in Immunology (Ed. Day and Good), Plenum, New York and London (1977); Am. J. Clin. Pathology, 68, 647–659 (1977).

The complement system can be considered to consist of three sub-systems: (1) a recognition unit (C1q) which enables it to combine with antibody molecules that have detected a foreign invader; (2) an activation unit (C1r, C1s, C2, (C4, C3) which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease dsseminated lupus erythematosus belongs in this category; its symptoms include nephritis, visceral lesions and skin eruptions. The treatment of diptheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969); Journal of Immunology, 119, 1–8, 1195, 1358–1364, 1482 (1977).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)benezenesulfonic acid], tetrasodium salt (chloroazol fast pink), heparin and a sulphated dextran have been reported to have an anticomplementary effect, British Journal of Experimental Pathology, 33, 327–339 (1952). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, Journal of Medicinal Chemistry, 12, 415–419; 902–905; 1049–1052; 1053–1056 (1969); Canadian Journal of Biochemistry, 47, 547–552 (1969); The Journal of Immunology, 104, 279–288 (1970); The Journal of Immunology, 106, 241–245 (1971); The Journal of Immunology, 111, 1061–1066 (1973); Biochim. Biophys. Acta, 317, 539–548 (1973); Life Sciences, 13, 351–362 (1973); Journal of Immunology, 113, 584 (1974); Immunology, 26, 819–829 (1974); Journal of Medicinal Chemistry, 17, 1160–1167 (1974); Biochim. Biophys. Res. Comm., 67, 225–263 (1975); Ann. N. Y. Acad. Sci., 256, 441–450 (1975); Journal of Medicinal Chemistry, 19, 634–639, 1079 (1976); Journal of Immunology, 118, 466 (1977); Arch. Int. Pharmacodyn., 226, 281–285 (1977); Biochem. Pharmacol. 26, 325–329 (1977); Journal Pharm. Sci., 66, 1367–1377 (1977); Chem. Pharm. Bull., 25, 1202–1208 (1977); Biochim. Biophys. Acta, 484, 417–422 (1977) and Journal Clin. Microbiology, 5, 278–284 (1977).

It has been reported that the known complement inhibitors epsilon-aminocaproic acid and tranexamic acid have been used with success in the treatment of hereditary angioneurotic edema, a disease state resulting from an inherited deficiency or lack of function of the serum inhibitor of the activated first component of complement (Cl inhibitor), The New England Journal of Medicine, 286, 808–812 (1972), 287, 452–454 (1972); Ann. Intern. Med., 84, 580–593 (1976); J. Allergy and Clin. Immunology, 60, 38–40 (1977).

It has also been reported that the drug pentosanpolysulfoester has an anticomplementary activity on human serum, both in vitro and in vivo, as judged by the reduction in total hemolytic complement activity; Pathologie Biologie, 25, 33–36, 25 (2), 105–108, 25 (3), 179–184 (1977).

It is known that the compound Suramin is moderately active as a complement inhibitor, and possesses the structure:

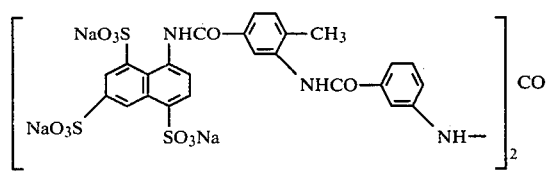

It now has been discovered that certain modifications of this structure provide compounds with enhanced inhibitory activity. This invention is based on such modifications.

The following publications, pertaining to the chemistry of Suramin, are related to the preparation of the novel compounds of this invention:

Bayer & Co., D.R.P. 278,122, June 22, 1913 [C.A. 9, 1096(1915)]

Bayer & Co., D.R.P. 288,272, Jan. 23, 1914 [C.A. 10, 2279(1916)]

Bayer & Co., D.R.P. 288,273, Feb. 21, 1914 [C.A. 10, 2279(1961)]

Frdl. 12, 185–186, 191–195 (1914–1916)

Danish Pat. No. 20,743 (1915)

Austrian Pat. No. 72,298 (1916)

Austrian Pat. No. 72,303 (1916)

U.S. Pat. No. 1,218,654 (1917)

U.S. Pat. No. 1,218,655 (1917)

Austrian Pat. No. 73,381 (1917)

U.S. Pat. No. 1,308,071 (1919)

E. Fourneau, J. Tréfouel, Mme. J. Tréfouel and J. Vallee, Acad. Sci. Comp. Rend., 178, 675–676 (1924)

E. Fourneau, F. Tréfouel and J. Vallee, Ann. de L'Institut Pasteur, 38 (2), 81–114 (1924)

B. Heymann, Zeitschrift Ang. Chem., 37, 585–589 (1924)

British Pat. No. 224,849 (1925)

U.S. Pat No. 1,606,624 (1926)

J. E. R. McDonagh, Brit. Med. J., 693–696 (1926) [Chem. Zentralblatt, 1769–1770 (1926 II)]

W. Roehl. Arch. Schiff. Trop. Hyg., 30 (1), 103–111 (1926)

Poulenc Fréres, D.R.P. 427,857, Apr. 20, 1926 [Frdl. 15, 1434–1436 (1928)]

I. E. Balaban and H. King, J. Chem. Soc., 3068–3097 (1927)

H. Bauer and J. Becker, Arb. Staatsinst. Exptl. Therap., 16 pp. (1928)

U.S. Pat. No. 1,968,820 (1934)

O. Yu. Magidson, O. S. Madaeva and M. V. Rubtzov, Khim. Farm. Prom., 2, 89–94 (1935) [C.A., 30, 4492 (1936)]

U.S. Pat. No. 2,126,180 (1938)

P. Pratsi and L. Raffa, Farmaco Sci e Tech (Pavia), 1, 21–34 (1946)

A. Spinks, Biochem. J., 42, 109–116 (1948)

E. D. Wills and A. Wormall, Biochem. J., 47, 158–170 (1950)

German Pat. No. 890,952 (1953) [C. A. 52, 14693 (1958)]

A. Adams, J. N. Ashley and H. Bader, J. Chem. Soc., 3739–3744 (1956) [C. A. 51, 4375i]

Publications related to the biological use of Suramin compounds for the purpose of inhibiting the complement system, including humans, as determined by the in vivo and in vitro testing of the blood serum of warm-blooded animals are:

B. Stuber and K. Lang, Arch. Exptl. Path. Pharmacol., 154, 41–49 (1930) [C. A. 25, 3067(1931)]

F. Klopstock, Zeitschrift fur Immunitatsforschung und experimentalle Therapie, 75, 348–354 (1932)

H. J. Schmid, Schweiz. Med. Woch., 96, 1267–1269 (1966)

K. Lauenstein, Bayer-Symposium I, 25–30 (1969)

J. S. C. Fong and R. A. Good, Clin. Exp. Immunol., 10, 127–138 (1972)

V. Eisen and C. Loveday, Br. J. Pharmac., 49, 678–687 (1973)

D. Brackertz and F. Kueppers, Allergol. Et Immunopath., 11, 163–168 (1974)

E. Raepple, H-U. Hill and M. Loos, Immunochemistry, 13 (3), 251–255 (1976)

SUMMARY OF THE INVENTION

This invention is concerned with ureylenebis[substituted-phenylenecarbonylimino-substituted-phenylenecarbonyliminonaphthalenetrisulfonic acids] and all pharmaceutically acceptable salts thereof, having complement inhibiting activity, which are new compounds of the general formulae:

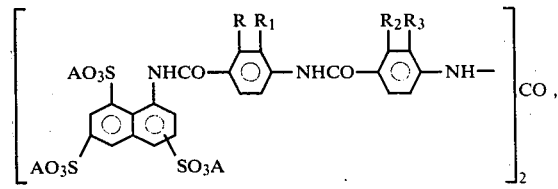

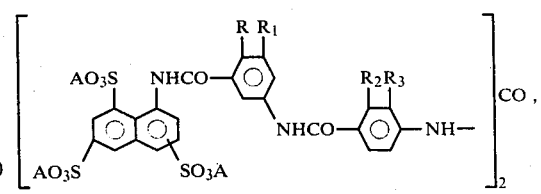

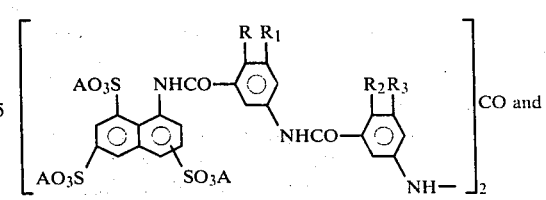

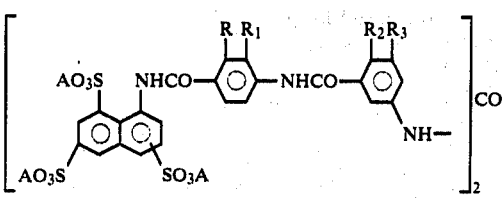

wherein R and $R_2$ are selected from the group consisting of hydrogen and —$SO_3A$, wherein A is a pharmaceutically acceptable salt cation; $R_1$ and $R_3$ are selected from the group consisting of hydrogen and —COOB, wherein B is selected from the group consisting of hydrogen and a pharmaceutically acceptable salt cation; with the proviso that R, $R_1$, $R_2$ and $R_3$ may not all be hydrogen; and with the second proviso that neither phenyl moiety can contain both —$SO_3A$ and —COOB.

A preferred embodiment of this invention consists of those compounds wherein either $R_1$ or $R_3$, or both, are —COOB; and R and $R_2$ are hydrogen.

Another preferred embodiment of this invention consists of those compounds wherein either R or $R_2$, or both, are —$SO_3A$; and $R_1$ and $R_3$ are hydrogen.

This invention is also concerned with compounds of the formulae:

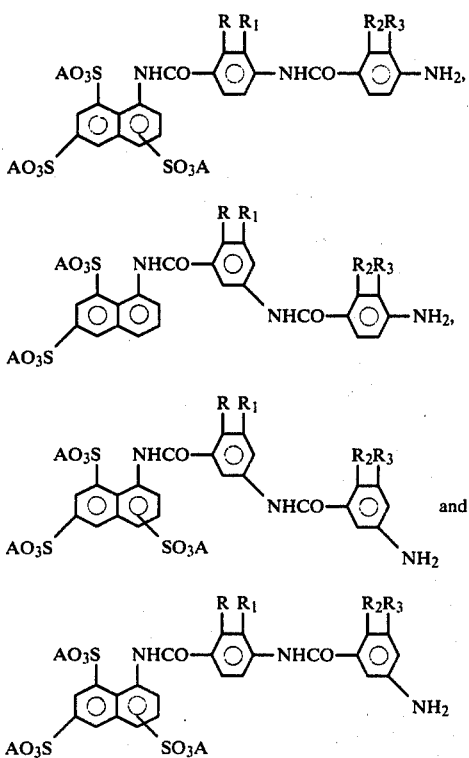

wherein R and $R_2$ are selected from the group consisting of hydrogen and —$SO_3A$, wherein A is a pharmaceutically acceptable salt cation; $R_1$ and $R_3$ are selected from the group consisting of hydrogen and —COOB, wherein B is selected from the group consisting of hydrogen and a pharmaceutically acceptable salt cation; with the proviso that R, $R_1$, $R_2$ and $R_3$ may not all be hydrogen; and with the second proviso that neither phenyl moiety can contain both —$SO_3A$ and —COOB; said compounds being useful as intermediates for the preparation of the complement inhibiting compounds described above. Some of the intermediate compounds also possess complement inhibiting activity.

DESCRIPTION OF THE INVENTION

The novel intermediate amine compounds of the invention are prepared by reacting the appropriate 8-amino-1,3,5- (and 1,3,6)naphthalenetrisulfonic acid, trialkali metal salt with a nitrosulfobenzoic acid anhydride such as 4-nitro-2-sulfobenzoic acid anhydride, or with a nitrobenzoyl chloride such as 3-carbomethoxy-5-nitrobenzoyl chloride for 10 minutes–19 hours in an alkaline aqueous media. After neutralization, the solution is diluted with absolute ethanol to provide the corresponding nitro-substituted-phenylenecarbonylimino-1,3,5(and 1,3,6)-naphthalenetrisulfonic acid, trialkali metal salt.

Hydrogenation of the preceding nitro compounds using 10% palladium-on-carbon catalyst, filtration, concentration and treatment with absolute ethanol provides the corresponding amino-substituted phenylenecarbonylimino-1,3,5 (and 1,3,6)-naphthalenetrisulfonic acid, trialkali metal salt. The amine compounds above, dissolved in alkaline aqueous media, are reacted once more with a nitrosulfobenzoic acid anhydride, or with a nitrobenzoyl chloride listed above for 10 minutes–19 hours. After neutralization, the aqueous solution is diluted with absolute ethanol to provide the corresponding nitro-substituted phenylenecarbonylimino, substituted phenylenecarbonylimino-1,3,5- (and 1,3,6)-naphthalenetrisulfonic acid, trialkali metal salt.

The above compounds, which contain the carbomethoxy substituent on the phenylene ring, are then converted to the corresponding free acids by stirring for 3 hours in 1 N sodium hydroxide solution. After acidification with dilute hydrochloric acid, the product is precipitated from water and ethanol.

The novel intermediate amine compounds of the invention are then obtained by hydrogenation of the corresponding nitro compounds using 10% palladium-on-carbon catalyst in water as previously described. Filtration and evaporation of the filtrate provides a residue which is dissolved in water and precipitated with absolute ethanol to provide the desired product.

The novel ureylene compounds of the invention, which are active complement inhibitors, are obtained by treating the intermediate amine compounds with phosgene in aqueous media made alkaline with alkali metal carbonate or pyridine. The solution is neutralized and the product is precipitated by the addition of alcohol.

This invention is concerned with a method of inhibiting the complement system in a body fluid, such as blood serum, which comprises subjecting body fluid complement to the action of an effective complement inhibiting amount of a compound encompassed within the formulae hereinabove. The method of use aspect of this invention is also concerned with a method of inhibiting the complement system in a warm-blooded animal which comprises administering to said animal an effective complement inhibiting amount of a compound encompassed within the formulae hereinabove. Body fluid can include blood, plasma, serum, synovial fluid, cerebrospinal fluid, or pathological accumulations of fluid such as pleural effusion, etc.

Compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of auto-allergic hemolytic anemia, certain kinds of platelet disorders and certain kinds of vasculitis. The compounds herein may also be used in the therapeutic treatment of warm-blooded animals having non-immunologic diseases such as paroxysmal nocturnal hemoglobinuria, hereditary antioneurotic edema (treated with Suramin, etc.) and inflammatory states induced by the action of bacterial or lysosomal enzymes on the appropriate complement components as for example, inflammation following coronary occulusion. They may also be useful in the treatment of transplant rejection and as blood culture or transport mediums.

The compounds of the present invention may be administered internally, e.g., orally or parenterally, e.g., intra-articularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

While in general the sodium salts of the acids of the invention are suitable for parenteral use, other salts may also be prepared, such as those of primary amines, e.g., ethylamine; secondary amines, e.g., diethylamine or diethanol amine; tertiary amines, e.g., pyridine or triethylamine or 2-dimethylaminomethyl-dibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore, as well as the sodium salt, those of the alkali metals, such as potassium and lithium; of ammonia; and of the alkaline earth metals, such as calcium or magnesium, may be employed. It will be apparent, therefore, that these salts embrace, in general, derivatives of salt-forming cations.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage from affording the advantage of prolonged or delayed action or predetermined successive cation of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristic of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test Code 035 (C3-C9 inhibitor)—This test determines the ability of the late components of human complement (C3-C9) to lyse EAC 142 in the presence of appropriate dilutions of the test compound. An active inhibitor protects EAC 142 from lysis by human C3-C9; (iii) Test Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test—Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test—Lethal shock is produced in guinea pigs by an i.v. injection of anti-Forssman antiserum and the harmonic mean death time of treated guinea pigs is compared with that of simultaneous controls; (vi) Complement Level Reduction Test—In this test, the above dosed guinea pigs, or others, are bled for serum and the complement level is determined in undiluted serum by the capillary tube method of U.S. Pat. No. 3,876,376 and compared to undosed control guinea pigs; and (viii) Cap 50 Test—Here, appropriate amounts of the test compound are added to a pool of guinea pig serum in vitro, after which the undiluted serum capillary tube assay referred to about is run. The concentration of compound inhibiting 50% is reported.

With reference to Table I. guinea pigs weighing about 300 g were dosed intravenously (i.v.) or intraperitoneally (i.p.) with 200 mg/kg of the test compound dissolved in saline and adjusted to pH 7-8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of tests code 026, 035, 036, Cap 50, % inhibition and Forssman shock. Table I shows that the compounds of the invention possess highly significant in vitro and in vivo complement inhibiting activity in warm-blooded animals are more active than the reference compound, Suramin. Results obtained are listed in Table I.

Table II shows the complement inhibiting activity of the intermediate compounds of the invention.

TABLE I

| | Biological Activities | | | | In Vivo Activity (Guinea Pig) % Inhibition | | | | | |
|---|---|---|---|---|---|---|---|---|---|---|
| | C1 026* | C-Late 035* | Shunt Inhibition 036* | | Intraperitoneal Time (minutes) | | | Intravenous Time (minutes) | | |
| Compound | Wells | Wells | Wells | Cap 50* | 30 | 60 | 120 | 2 | 30 | 120 |
| Suramin | +4** | +2** | | 361 | −9 | −17 | −44 | | | |
| 8,8'-[Ureylenebis[(2--sulfo-4,1-phenylene-carbonyl)imino](2-sulfo--4,1-phenylenecarbonyl)imino]]di-1,3,6-naphthalenetrisulfonic acid, decasodium salt | +8 | +1 | +5** +3 | 270 | −68 | −24 | −14 | | | |
| 8,8'-[Ureylenebis[(2-sulfo-4,1-phenylene-carbonyl)imino(2-sulfo-4,1-phenylenecarbonyl) +7 imino]]di-1,3,5-naphthalenetrisulfonic acid, decasodium salt | +1 | +4 | 113 | −31 | −36 | −58 | −38 | −47 | −22 | |
| 5,5'-[Ureylenebis[(2-sulfo-4,1-phenylenecarbonyl)imino]]bis[N-4,6,8-trisulfo-1-naphthylisophthalamic acid], octasodium salt | +6 | +2 | +5 | 83 | | | | | | |
| 5,5'-Ureylenebis[N-[3-carboxy-5-(4,6,8-trisulfo-1-naphthylcarbamoyl)phenyl]isophthalamic acid], decasodium salt | +6 | +2 | +4 | | −86 | −89 | −96 | | | |
| 5,5' Ureylenebis[N-[3-carboxy-5-(4,6,8-trisulfo-1-naphthylcarbamoyl)phenyl]isophthalamic acid], hexasodium salt | +5 | +2 | +3 | 17 | | | | | | |

*Code designation for tests employed as referred herein.
**Activity in wells a serial diluteion assay. Higher well number indicates higher activity. The serial dilutions are two-fold.
N = Negative (no activity)

TABLE II (Intermediates)

| Compound | Biological Activites | | | | In Vivo Activity (Guinea Pig) % Inhibition | | | | | |
|---|---|---|---|---|---|---|---|---|---|---|
| | Cl 026* Wells | C-Late 035* Wells | Shunt Inhibition 036* Wells | Cap 50* | Intraperitoneal Time (minutes) | | | Intravenous Time (minutes) | | |
| | | | | | 30 | 60 | 120 | 2 | 30 | 120 |
| 8-[4-(4-Amino-2-sulfobenzamido)-2-sulfobenzamido]-1,3,6-naphthalenetrisulfonic acid, pentasodium salt | +5** | N | N | 420 | | | | −77 | −43 | −31 |
| 8-[4-(4-Amino-2-sulfobenzamido)-2-sulfobenzamido]-1,3,5-naphthalenetrisulfonic acid, pentasodium salt | +4 | N | N | 177 | −15 | −17 | −23 | −52 | −28 | −10 |
| 5-(4-Amino-2-sulfobenzamido)-N-(4,6,8-trisulfo-1-naphthyl)isophthalamic acid, tetrasodium salt | +3 | N | N | 242 | | | | | | |
| 5-Amino-3'-carboxy-5'-(4,6,8-trisulfo-1-naphthylcarbamoyl)isophthalanilic acid, trisodium salt | +3 | N | N | 107 | | | | | | |

*Code designation for tests employed as referred herein.
**Activity in wells a serial dilution assay. Higher well number indicates higher activity. The serial dilutions are two-fold.
N = Negative (no activity).

EXAMPLE 1

8-[4-(4-Amino-2-sulfobenzamido)-2-sulfobenzamido]-1,3,6-naphthalenetrisulfonic acid pentasodium salt

A solution of 100 g of 5-nitro-o-toluenesulfonic acid in 600 ml of water plus 80 ml of 5 N sodium hydroxide is heated to 90° C. in a 2 liter Erlenmeyer flask, then 240 g of potassium permanganate is added portionwise to maintain reflux over one hour and 15 minutes. The mixture is filtered and the residue is washed with water. The combined filtrate and washings are concentrated in vacuo and allowed to crystallize to give 86.2 g of crude 4-nitro-2-sulfobenzoic acid, sodium potassium salt. Recrystallization from water gives 71.3 g of purified product.

The total product above is dissolved in 250 ml of water plus 35 ml concentrated hydrochloric acid by warming on a steam bath. The solution is then diluted with 300 ml of ethanol and allowed to crystallize at room temperature. The mixture is allowed to stand 48 hours in a chill room, then is filtered. The precipitate is washed with cold 50% aqueous ethanol, then with ethanol and ether. The material is recrystallized from 200 ml of water and is dried at 110° C. to give 52.0 g of 4-nitro-2-sulfobenzoic acid-2-sodium salt.

A 50.0 g portion of the preceding compound and 500 g of thionyl chloride is stirred and refluxed for 19 hours. The mixture is evaporated to dryness in vacuo and the residue is warmed with 300 ml of toluene and is filtered. The filtrate is concentrated in vacuo and the product is crystallized twice from toluene to give 30.4 g of 4-nitro-2-sulfobenzoic acid anhydride.

To an ice bath cooled solution (5° C.) of 16.0 g of 8-amino-1,3,6-naphthalenetrisulfonic acid trisodium salt and 6.7 g of sodium acetate trihydrate in 100 ml of water is added 8.8 g of 4-nitro-2-sulfobenzoic acid anhydride. The mixture is stirred vigorously for 10 minutes and is filtered. The filtrate is cooled in an ice bath and diluted with 500 ml of cold ethanol. The mixture is filtered and the product is washed with ethanol and ether and then is dried. The product is dissolved in 50 ml of warm water and is stirred for 10 minutes after the addition of one ml of acetone. The mixture is treated with activated charcoal, filtered through diatomaceous earth and is washed with 20 ml of water. The filtrate is cooled in an ice bath and acidified with 1.5 ml of concentrated hydrochloric acid. The solution is diluted with 500 ml of cold ethanol and the precipitated material is filtered, washed with ethanol followed by ether and dried. The above purification process is repeated without acidification. The product obtained is dried overnight at 110° C. to give 18.5 g of 8-(4-nitro-2-sulfobenzamido)-1,3,6-naphthalenetrisulfonic acid tetrasodium salt.

A 17.5 g portion of the preceding product and 1.5 g of palladium-on-carbon catalyst in 150 ml of water is hydrogenated for one hour at room temperature, then is filtered through diatomaceous earth. The filtrate is concentrated and the product is precipitated by the addition of absolute ethanol. The product is collected and dried overnight in an abderhalden apparatus at 110° C. to give 14.5 g of 8-(4-amino-2-sulfobenzamido)-1,3,6-naphthalenetrisulfonic acid tetrasodium salt as an off-white powder.

To an ice bath cooled solution (5° C.) of 17.2 g of the preceding product (prepared as described above) and 5.24 g of sodium acetate trihydrate in 100 ml of water is added, in one portion, 6.87 g of 4-nitro-2-sulfobenzoic acid anhydride. The mixture is stirred for 10 minutes, treated with activated charcoal, and filtered through diatomaceous earth. The filtrate is poured into 750 ml of absolute ethanol in a baffle flask with vigorous stirring. The mixture is filtered and the product is washed with ethanol and ether and is dried in vacuo. The product is dissolved in 100 ml of water, acidified with 3.0 ml of concentrated hydrochloric acid and is poured into 500 ml of ice-cold absolute ethanol in a baffle flask, with vigorous stirring. The product is collected by filtration, washed wtih ethanol and ether, and dried to yield 19.35 g of 8-[4-(4-nitro-2-sulfobenzamido)-2-sulfobenzamido]-1,3,6-naphthalenetrisulfonic acid pentasodium salt.

A 17.5 g portion of the product above and 1.0 g of 10% palladium-on-carbon catalyst in 100 ml of water is hydrogenated for one hour in a Parr shaker. The mixture is filtered through diatomaceous earth. The filtrate is concentrated to 65.0 ml and is poured into 500 ml of vigorously stirred absolute ethanol in a baffle flask, resulting in formation of a granular precipitate and a milky suspension. The suspension is decanted and set aside. The precipitate is filtered and washed with ethanol and ether to yield 16.5 g of product.

The above suspension is filtered through diatomaceous earth and the collected material is dissolved off the filter with water. The aqueous solution is concentrated to 10 ml and poured into 100 ml of vigorously stirred ethanol to precipitate 2.26 g of additional product which is collected and washed as above. The product fractions are combined and dried to give 15.3 g of the product of the Example as a pale tan powder.

EXAMPLE 2

8,8'-[Ureylenebis[(2-sulfo-4,1-phenylenecarbonyl)-imino](2-sulfo-4,1-phenylenecarbonyl)imino]di-1,3,6-naphthalenetrisulfonic acid, decasodium salt A 7.13 g portion of the product of Example 1 is diluted with 40 ml of water, 4.0 ml of pyridine is added and phosgene is passed through for 2-3 minutes until the solution is weakly acidic. An additional 0.4 ml of pyridine is added to neutralize the solution, then the solution is poured into 350 ml of vigorously stirred ethanol. The resulting solid is separated and washed with ethanol and ether to give a pink product. The product is dissolved in 25 ml of water. The pH of the solution is adjusted to 9.0 with 2.8 ml of 5 N sodium hydroxide and the volume is adjusted to 50 ml with water. The solution is treated with activated charcoal and filtered through diatomaceous earth. The filter is washed with 40 ml of water. The combined filtrate and washings are cooled in an ice bath and gradually diluted with 800 ml of cold absolute ethanol to give a milky solution containing a gum. The mixture is stirred in an ice-bath for 3 hours. The product is separated, pulverized and dried to yield 5.0 g of the product of the Examples as a tan powder.

EXAMPLE 3

8-[4-(4-Amino-2-sulfobenzamido)-2-sulfobenzamido]-1,3,5-naphthalenetrisulfonic acid, pentasodium salt To a warm solution of 23.8 g of 80.5% 8-amino-1,3,5-naphthalenetrisulfonic acid in 25 ml of water and 25 ml of 5 N sodium hydroxide is slowly added 125 ml of absolute ethanol with vigorous stirring. The mixture is cooled to room temperature, is filtered and washed with 50 ml of 80% aqueous ethanol, then ethanol and ether. The material is dried ovenight at 110° C. to give 21.0 g of 8-amino-1,3,5-naphthalenetrisulfonic acid, trisodium salt as a grey powder.

A 4.49 g portion of the material above and 2.14 g of sodium acetate trihydrate is dissolved in 30 ml of water. The solution is cooled to 0° C. in an ice bath and 2.72 g of 4-nitro-2-sulfobenzoic acid anhydride is added all at once. After a few minutes, the ice bath is removed and the solution is stirred for a total of 20 minutes. The solution is filtered and the filtrate acidified with 0.88 ml of concentrated hydrochloric acid. The solution is concentrated and the residue is dissolved in 10 ml of water, then is added to 200 ml of ethanol and is stirred for ½ hour. The precipitate is collected by filtration and washed with ethanol and ether and is dried in vacuo.

The dried material is dissolved in 10 ml of hot water and 50 ml of absolute ethanol is added, with stirring for ½ hour. An additional 20 ml of ethanol is added, with stirring continued for 10 minutes. The precipitate is then collected by filtration, washed with ethanol and ether and dried in an Abderhalden apparatus at 110° C. overnight to yield 4.5 g of product. The product is recycled through the procedure described above using 1.07 g of sodium acetate trihydrate, 1.36 g of 4-nitro-2-sulfobenzoic acid anhydride and 0.44 ml of concentrated hydrochloric acid, respectively. After the material is dried in vacuo ad previously described, the dried material is dissolved in 10 ml of hot water and 70 ml of ethanol is added slowly with stirring at room temperature for one hour. The precipitate is collected by filtration and is washed with 80% aqueous ethanol, ethanol and ether, then is dried as previously described to afford 4.5 g of 8-(p-nitro-2-sulfobenzamido)-1,3,5-naphthalenetrisulfonic acid, tetrasodium salt as a yellow solid.

A 3.9 g portion of the above compound and 400 mg of 10% palladium-on-carbon catalyst in 50 ml of water is hydrogenated, filtered and evaporated as described in Example 3. The residue obtained is dissolved in 10 ml of hot water and 100 ml of absolute ethanol is added. An oily precipitate is formed which is redissolved by addition of more ethanol. The solvent is then removed in vacuo to give 3.7 g of 8-(4-amino-2-sulfobenzamido)-1,3,5-naphthalenetrisulfonic acid tetrasodium salt.

To a stirred solution of 6.9 g of the preceding product and 2.15 g of sodium acetate trihydrate, in 45 ml of water at room temperature, is added 2.76 g of 4-nitro-2-sulfobenzoic acid anhydride. The mixture is stirred for one hour and filtered. The filtrate is acidified with 0.88 ml of concentrated hydrochloric acid and evaporated. The residue is dissolved in 25 ml of hot water and 100 ml of absolute ethanol is added with stirring. The solid is collected and washed with 80% ethanol. The solid is slurried with absolute ethanol, filtered, washed with ether and dried to yield 7.05 g of 8-[4-(4-nitro-2-sulfobenzamido)-2-sulfobenzamido]-1,3,5-naphthalenetrisulfonic acid, pentasodium salt.

A mixture of 6.35 g of the above product, 100 ml of water and 0.9 g of 10% palladium-on-carbon catalyst is hydrogenated on a Parr shaker until no additional hydrogen is absorbed. The reaction mixture is filtered through diatomaceous earth and the filtrate is evaporated. The residue is dissolved in 25 ml of hot water and absolute ethanol is added with stirring providing a gum. The supernatant is decanted and the gum is triturated with hot ethanol to yield a solid. The solid is collected, washed with ethanol and ether and dried to yield 5.25 g of the product of the Example.

EXAMPLE 5

5-(4-Amino-2-sulfobenzamido)-N-(4,6,8-trisulfo-1-naphthyl)isophthalamic acid, tetrasodium salt A mixture of 60.0 g of 5-nitroisophthalic acid, 300 ml of thionyl chloride and one ml of dimethylformamide is stirred at room temperature for 30 minutes, then is refluxed for one hour. The resulting clear solution is allowed to stand 24 hours, then is evaporated to a small volume in vacuo. The evaporation step is repeated with toluene and the resulting liquid is diluted with 250 ml of hexane. The mixture is stirred and cooled until the resulting oil is solidified. The product is ground to a powder and is recrystallized twice from carbon tetrachloride to give 47.4 g of 5-nitroisophthaloyl chloride.

A 35.0 g portion of 5-nitroisophthaloyl chloride is added to 600 ml of methanol with stirring producing a precipitate. The mixture is heated to solution, then is chilled, filtered and dried to yield 31.75 g of dimethyl 5-nitroisophthalate.

A mixture of 7.46 g of potassium hydroxide in 87.5 ml of methanol is added to a stirred solution of 31.75 g of the preceding product in 331.0 ml of acetate. A solid is precipitated and stirring is continued for 16 hours. The solid (A) is filtered off, washed with ether and set aside. The filtrate is evaporated, the residue is extracted with 125 ml of warm water and is filtered. The filtrate is acidified with dilute hydrochloric acid to produce a precipitate which is collected and dried to yield 3.4 g of product. The solid (A) above is extracted with 250 ml of warm water and is filtered. The filtrate is filtered again at room temperature, acidified with dilute hydrochloric acid and cooled. The precipitate is collected and dried to give 18.25 g of additional product identified as 5-nitro-isophthalic acid, 3-methyl ester.

A mixture of 18.38 g of the product above, 60 ml of thionyl chloride and 0.37 ml of dimethylformamide is heated at 60° C. for 2.5 hours. The solution is evaporated, then is treated with toluene, and again is evaporated. The residue is slurried in hot diethyl ether and the ether volume is reduced by evaporation. The mixture is chilled and filtered. The precipitate is washed with cold ether and is dried. The material is extracted with 500 ml of boiling hexane by decantation. The hexane is cooled and filtered to yield 14.1 g of 3-carbomethoxy-5-nitrobenzoyl chloride.

To a solution of 3.5 g of 8-amino-1,3,5-naphthalenetrisulfonic acid, trisodium salt (prepared as described in Example 3) and 2.24 g of sodium acetate trihydrate in 40 ml of water is added, with stirring, 2.0 g of 3-carbomethoxy-5-nitrobenzoyl chloride. Stirring is continued for one hour, then 4.0 ml of ethyl ether is added and stirring is continued for 2 hours longer. The solution is filtered and the filtrate is concentrated. The residue is dissolved in 20 ml of hot water and on addition of 20 ml of absolute ethanol a precipitate is formed. The precipitate is mobilized with water and is filtered and washed with 80% aqueous ethanol, ethanol and ether. The filtrate is allowed to stand overnight to afford additional product which is collected and washed as above. The combined product is dried by conventional means to yield 3.3 g of 5-nitro-N-4,6,8-trisulfo-1-naphthylisophthalamic acid methyl ester, trisodium salt.

A 3.27 g portion of the preceding product and 700 mg of 10% palladium-on-carbon catalyst in 100 ml of water is hydrogenated in a Parr shaker until no more hydrogen is absorbed. The resulting mixture is filtered through diatomaceous earth and the filtrate is concentrated. The residue is dissolved in about 15 ml of hot water and absolute ethanol is added to a total volume of 250 ml with formation of a precipitate. The precipitate is collected by filtration, washed with ethanol and ether and dried to yield 2.4 g of 5-amino-N-4,6,8-trisulfo-1-naphthylisophthalamic acid methyl ester, trisodium salt as a powder.

To a stirred solution of 1.43 g of the above product, 244 mg of anhydrous sodium carbonate and 15.0 ml of water is added 642 mg of 4-nitro-2-sulfobenzoic acid anhydride, stirring is continued at room temperature for 16 hours. The resulting mixture is acidified with dilute hydrochloric acid, then ethanol is added and the solution is evaporated in vacuo. The residue is dissolved in a small amount of hot water and triturated with ethanol until cloudiness persists. The mixture is allowed to cool with separation of crystals. The crystals are collected, washed twice with ethanol and ether and air dried to yield 1.82 g of 5-(p-nitro-2-sulfobenzamido)-N-(4,6,8-trisulfo-1-naphthyl)isophthalamic acid methyl ester, tetrasodium salt.

A solution of 1.6 g of the preceding product in 25.0 ml of 1 N sodium hydroxide is stirred at room temperature for 3 hours. The solution is acidified with dilute hydrochloric acid, then ethanol is added and the solution is evaporated in vacuo. The residue is dissolved in hot water and triturated with ethanol until cloudy. The mixture is allowed to cool and the resulting precipitate is collected by filtration, washed twice with ethanol and ether and air dried to provide 1.34 g of 5-(4-nitro-2-sulfobenzamido)-N-(4,6,8-trisulfo-1-naphthyl)isophthalamic acid, tetrasodium salt.

A mixture of 1.15 g of the above compound, 160 ml of water and 115 mg of 10% palladium-on-carbon catalyst is hydrogenated in a Parr shaker for 3 hours. The resulting mixture is filtered through diatomaceous earth. Ethanol is added to the filtrate and the solution is evaporated. The residue is dissolved in a small amount of water, then ethanol is added with separation of a solid. The solid is collected and dried to yield 890 mg of the product of the Example as a white powder.

EXAMPLE 6

5,5'-[Ureylenebis[(2-sulfo-4,1-phenylenecarbonyl)imino]]bis[N-4,6,8-trisulfo-1-naphthylisophthalamic acid], octasodium salt A solution of 690 mg of the product of Example 7 and 220 mg of anhydrous sodium carbonate in 20 ml of water is phosgenated at a slow rate until it is acidic to Congo Red indicator paper. The mixture is evaporated and the residue is dissolved in a minimum amount of water, ethanol is added the the resulting solid is collected by filtration. The solid (620 mg) is dissolved in 6.0 ml of water and is phosgenated again as above in the presence of 220 mg of anhydrous sodium carbonate. Ethanol is added to the resulting mixture which is then evaporated. The residue is dissolved in water and reprecipitated with ethanol. This step is repeated, then the final product is collected, washed twice with ethanol and ether and dried to yield 290 mg of the product of the Example as a white powder.

EXAMPLE 7

5-Amino-3'-carboxy-5'-(4,6,8-trisulfo-1-naphthylcarbamoyl)isophthalanilic acid, trisodium salt To a stirred solution of 1.8 g of 5-amino-N-4,6,8-trisulfo-1-naphthylisophthalamic acid methyl ester trisodium salt (prepared as described in Example 5), 15.0 ml of water and 305 mg of anhydrous sodium carbonate is added 837 mg of 3-carbomethoxy-5-nitrobenzoyl chloride (prepared as in Example 5). Additional water is added to facilitate stirring. The mixture is stirred for 3 hours and is acidified with dilute hydrochloric acid to give complete solution. Ethanol is added to the solution with stirring to provide a white precipitate. The precipitate is collected, washed with ethanol and ether and air dried. The product is reprecipitated from water and ethanol, then is collected and is washed twice with ethanol and ether and dried to yield 1.68 g of 3'-carboxy-5-nitro-5'-(4,6,8-trisulfo-1-naphthylcarbamoyl)isophthalanilic acid dimethyl ester, trisodium salt.

A solution of the entire product above and 50.0 ml of 1 N sodium hydroxide is stirred at room temperature for 3 hours. The solution is acidified with dilute hydrochloric acid, then absolute ethanol is added and the solution is evaporated. The residue is dissolved in hot water, triturated with ethanol and cooled. The precipitate is collected and washed twice with both ethanol and ether then is dried to afford 930 mg of 3'-carboxy-5'-(4,6,8-trisulfo-1-naphthylcarbamoyl)-5-nitroisophthalanilic acid, trisodium salt.

A mixture of 730 mg of the preceding compound, 100 ml of water and 75.0 mg of 10% palladium-on-carbon catalyst is hydrogenated on a Parr shaker for 4 hours. The resulting mixture is filtered through diatomaceous earth and the filtrate is evaporated. The residue is dissolved in hot water, then absolute ethanol is added and a precipitate is formed on cooling to room temperature. The precipitate is collected by filtration and is washed twice with both ethanol and ether. The material is dried to yield 520 mg of the product of the Example as a tan powder.

EXAMPLE 8

5,5'-Ureylenebis[N-[3-carboxy-5-(4,6,8-trisulfo-1-naphthaylcarbamoyl)phenyl]isophthalamic acid], decasodium salt A solution of 390 mg of the product of Example 7 and 55.0 mg of sodium carbonate in 10 ml of water is phosgenated until it becomes acidic. The resulting milky solution is neutralized with sodium carbonate and is evaporated. The residue is dissolved in water and absolute ethanol is added to provide a precipitate. The precipitate is collected and washed twice with both ethanol and ether, then is dried to yield 261 mg of the product of the Example as a white powder.

EXAMPLE 9

5,5'-Ureyelenbis[N-[3-carboxy-5-(4,6,8-trisulfo-1-naphthylcarbamoyl)phenyl]isophthalamic acid]hexasodium salt A 125 mg portion of the product of Example 10 is dissolved in 5 ml of water and is then acidified with glacial acetic acid. Absolute ethanol is added to precipitate a product. The product is collected by filtration, then is washed with ethanol and ether and is dried to yield 92 mg of the product of the Example as a pale yellow powder.

EXAMPLE 10

5-Amino-3'-carboxy-5'-(3,5,8-trisulfo-1-naphthylcarbamoyl)isophthalanilic acid, trisodium salt Following the procedure of Example 7, employing 5-amino-N-3,6,8-trisulfo-1-naphthylisophthalamic acid methyl ester, trisodium salt (prepared as described in Examples 3 and 5 using 8-amino-1,3,6-naphthalenetrisulfonic acid, trisodium salt) provides the product of the Example.

EXAMPLE 11

5,5'-Ureylenebis[N-[3-carboxy-5-(3,6,8-trisulfo-1-naphthylcarbamoyl)phenyl]isophthalamic acid], decasodium salt Following the procedure of Example 8, phosgenation of the product of Example 10 provides the product of the Example.

EXAMPLE 12

5-Amino-3'-sulfo-5'-(4,6,8-trisulfo-1-naphthylcarbamoyl)isophthalanilic acid, tetrasodium salt Following the procedure of Example 1, 4-nitro-2-sulfobenzoic acid anhydride is reacted with 8-amino-1,3,5-naphthalenetrisulfonic acid, trisodium salt, the product therefrom being reduced to provide 8-(4-amino-2-sulfobenzamido)-1,3,5-naphthalenetrisulfonic acid, tetrasodium salt. Reaction of the latter with 3-carbomethoxy-5-nitrobenzoyl chloride (prepared as described in Example 5), followed by hydrolysis and reduction gives the product of the Example.

EXAMPLE 13

5,5''-Ureylenebis[3'-sulfo-4'-(4,6,8-trisulfo-1-naphthylcarbamoyl) isophthalanilic acid], decasodium salt Following the procedure of Example 8, phosgenation of the product of Example 12 provides the product of the Example.

EXAMPLE 14

| Preparation of Compressed Tablet | |
| --- | --- |
| Ingredient | mg/Tablet |
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 15

| Preparation of Compressed Tablet - Sustained Action | |
| --- | --- |
| Ingredient | mg/Tablet |
| Active Compound as Aluminum Lake*, Micronized | 0.5–500 (as acid equivalent) |
| Dibasic Calcium Phophate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 16

| Preparation of Hard Shell Capsule | |
| --- | --- |
| Ingredient | mg/Capsule |
| Active Compound | 0.5–500 |
| Lactose, Spray Dried | qs |
| Magnesium Stearate | 1–10 |

EXAMPLE 17

Preparation of Oral Liquid (Syrup)

| Ingredient | % W/V |
|---|---|
| Active Compound | 0.05-5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 18

Preparation of Oral Liquid (Elixir)

| Ingredient | % W/V |
|---|---|
| Active Compound | 0.05-5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 19

Preparation of Oral Suspension (Syrup)

| Ingredient | % W/V |
|---|---|
| Active Compound as Aluminum Lake, Micronized | 0.05-5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 20

Preparation of Injectable Solution

| Ingredient | % W/V |
|---|---|
| Active Compound | 0.05-5 |
| Benzyl Alcohol N.F. | 0.9 |
| Water for Injection | 100.0 |

EXAMPLE 21

Preparation of Injectable Oil

| Ingredient | % W/V |
|---|---|
| Active Compound | 0.05-5 |
| Benzyl Alcohol | 1.5 |
| Sesame Oil qs ad | 100.0 |

EXAMPLE 22

Preparation of Intra-Articular Product

| Ingredient | Amount |
|---|---|
| Active Compound | 2-20 mg |
| NaCl (physiological saline) | 0.9% |
| Benzyl Alcohol | 0.9% |
| Sodium Carboxymethylcellulose | 1-5% |
| pH adjusted to 5.0-7.5 | |

Preparation of Intra-Articular Product -continued

| Ingredient | Amount |
|---|---|
| Water for Injection qs ad | 100% |

EXAMPLE 23

Preparation of Injectable Depo Suspension

| Ingredient | % W/V |
|---|---|
| Active Compound | 0.05-5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6-8 | qs |
| Water for Injection qs ad | 100.0 |

EXAMPLE 24

Preparation of Dental Paste

| Ingredient | % W/V |
|---|---|
| Active Compound | 0.05-5 |
| Zinc Oxide | 15 |
| Polyethylene Glycol 4000 USP | 50 |
| Distilled Water qs | 100 |

EXAMPLE 25

Preparation of Dental Ointment

| Ingredient | % W/V |
|---|---|
| Active Compound | 0.05-5 |
| Petrolatum, White USP qs | 100 |

EXAMPLE 26

Preparation of Dental Cream

| Ingredient | % W/V |
|---|---|
| Active Compound | 0.05-5 |
| Mineral Oil | 50 |
| Beeswax | 15 |
| Sorbitan Monostearate | 2 |
| Polyoxyethylene 20 Sorbitan Monostearate | 3 |
| Methylparaben USP | 0.18 |
| Propyl Paraben USP | 0.02 |
| Distilled Water qs | 100 |

EXAMPLE 27

Preparation of Topical Cream

| Ingredient | % W/W |
|---|---|
| Active Compound | 0.05-5 |
| Sodium Laurylsulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 28

| Preparation of Topical Ointment | |
|---|---|
| Ingredient | % W/W |
| Active Compound | 0.05–5 |
| Cholesterol | 3 |
| Stearyl Alcohol | 3 |
| White Wax | 8 |
| Petrolatum, White USP qs | 100 |

EXAMPLE 29

| Preparation of Spray Lotion (non-Aerosol) | |
|---|---|
| Ingredient | % W/W |
| Active Compound | 0.05–5 |
| Isopropyl Myristate | 20 |
| Alcohol (Denatured) qs | 100 |

EXAMPLE 30

| Preparation of Buccal Tablet | |
|---|---|
| Ingredient | g/Tablet |
| Active Ingredient | 0.00325 |
| 6 × Sugar | 0.29060 |
| Acacia | 0.1453 |
| Soluble Starch | 0.1453 |
| F. D. & C. Yellow No. 6 Dye | 0.00049 |
| Magnesium Stearate | 0.00160 |
| | 0.32500 |

The final tablet will weigh about 325 mg. and may be compressed into buccal tablets in flat faced or any other tooling shape convenient for buccal administration.

EXAMPLE 31

| Preparation of Lozenge | |
|---|---|
| Ingredient | g/Lozenge |
| Active Ingredient | 0.0140 |
| Kompact ® Sugar (Sucrest Co.) | 0.7138 |
| 6 × Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝″ flat based lozenge tooling. Other shapes may also be utilized.

We claim:

1. A compound of the formulae:

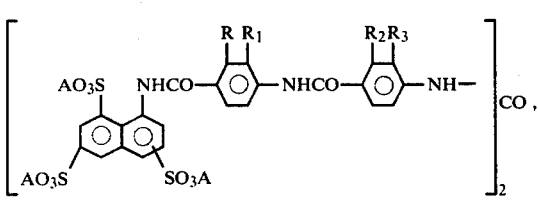

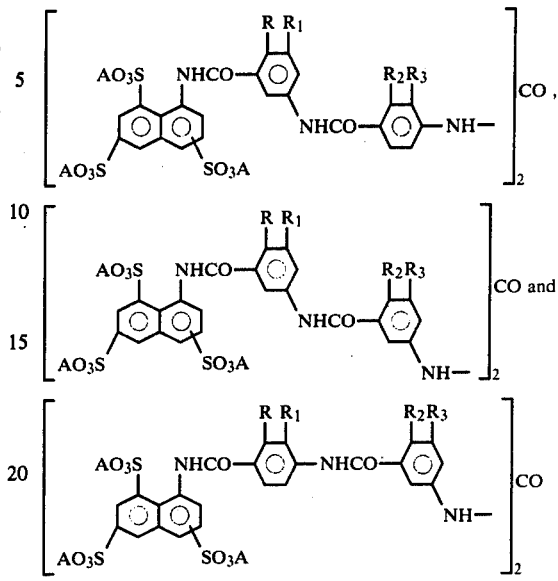

wherein R and $R_2$ are selected from the group consisting of hydrogen and $-SO_3A$ wherein A is a pharmaceutically acceptable salt cation; $R_1$ and $R_3$ are selected from the group consisting of hydrogen and $-COOB$, wherein B is selected from the group consisting of hydrogen and a pharmaceutically acceptable salt cation; with the proviso that R, $R_1$, $R_2$ and $R_3$ may not all be hydrogen; and with the second proviso that when R is $-SO_3A$, $R_1$ may not be $-COOB$ and when $R_2$ is $-SO_3A$, $R_3$ may not be $-COOB$.

2. A compound according to claim 1, wherein either $R_1$ or $R_3$, or both, are $-COOB$; and R and $R_2$ are hydrogen.

3. A compound according to claim 1, wherein either R or $R_2$, or both, are $-SO_3A$; and $R_1$ and $R_3$ are hydrogen.

4. The compound according to claim 1, 8,8′-[Ureylenebis[(2-sulfo-4,1-phenylenecarbonyl)imino(2-sulfo-4,1-phenylenecarbonyl)imino]]di-1,3,6-naphthalenetrisulfonic acid, decasodium salt.

5. The compound according to claim 1, 8,8′-[Ureylenebis[(2-sulfo-4,1-phenylenecarbonyl)imino(2-sulfo-4,1-phenylenecarbonyl)imino]]di-1,3,5-naphthalenetrisulfonic acid, decasodium salt.

6. The compound according to claim 1, 5,5′-[Ureylenebis[(2-sulfo-4,1-phenylenecarbonyl)imino]]-bis[4-4,6,8-trisulfo-1-naphthylisophthalamic acid], octasodium salt.

7. The compound according to claim 1, 5,5′-Ureylenebis[N-[3-carboxy-5-(4,6,8-trisulfo-1-naphthylcarbamoyl)phenyl] isophthalamic acid], decasodium salt.

8. The compound according to claim 1, 5,5′-Ureylenebis[N-[3-carboxy-5-(4,6,8-trisulfo-1-naphthylcarbamoyl)phenyl] isophthalamic acid], hexasodium salt.

9. The compound according to claim 1, 5,5′-Ureylenebis[N-[3-carboxy-5-(3,6,8-trisulfo-1-naphthylcarbamoyl)phenyl] isophthalamic acid], decasodium salt.

10. The compound according to claim 1, 5,5″-Ureylenebis[3′-sulfo-4′-(4,6,8-trisulfo-1-naphthylcarbamoyl)isophthalanilic acid], decasodium salt.

* * * * *